United States Patent [19]

Oppawsky et al.

[11] Patent Number: 5,266,777
[45] Date of Patent: Nov. 30, 1993

[54] DENTAL FURNACE WITH METALLIC INNER HOUSING, PLASTIC OUTER HOUSING, AND AIR SPACE THEREBETWEEN

[75] Inventors: Steffen Oppawsky, Bad Homburg; Peter Gernhard, Friedrichsdorf, both of Fed. Rep. of Germany

[73] Assignee: Heraeus Kulzer GmbH, Hanau, Fed. Rep. of Germany

[21] Appl. No.: 839,207

[22] Filed: Feb. 20, 1992

[30] Foreign Application Priority Data

Feb. 25, 1991 [DE] Fed. Rep. of Germany ....... 4105845

[51] Int. Cl.⁵ ............................................. A61C 13/20
[52] U.S. Cl. .................................. 219/400; 219/390; 432/120; 432/207
[58] Field of Search ............... 219/400, 390, 385, 386, 219/521; 432/120, 207; 433/32

[56] References Cited

U.S. PATENT DOCUMENTS

| | | | |
|---|---|---|---|
| 2,002,241 | 5/1935 | Forde | 219/390 |
| 2,179,256 | 11/1939 | Gill | 219/400 |
| 2,836,696 | 5/1958 | Ratchford | 219/386 |
| 2,969,450 | 1/1961 | Bernstein | 219/400 |
| 3,313,917 | 4/1967 | Ditzler | 219/400 |
| 4,396,825 | 8/1983 | Cox | 219/521 |
| 4,865,864 | 9/1989 | Rijswijck | 219/400 |

OTHER PUBLICATIONS

Kulzer, "Silicoater MD, the Kulzer Silicoater Method for Manufacture of a Fissure-Free Plastic-to-Metal Bond in Dentistry", Brochure No. 90 590/D 260 S K dt., pp. 2-7, pub. May 1990.

*Primary Examiner*—Bruce A. Reynolds
*Assistant Examiner*—John A. Jeffery
*Attorney, Agent, or Firm*—Frishauf, Holtz, Goodman & Woodward

[57] ABSTRACT

A dental furnace for heat treatment of dental materials and dental components, particularly for firing these at temperatures over 100° C. comprises an insulated furnace space which can be closed off by a door. The furnace space has a housing which is suspended in an inner housing of metal; the inner housing is supported by a multi-part outer housing, and the door is pivotably fastened on the inner housing. In order to satisfy the requirements of firing at up to 400° C., and to achieve a simple, cost-effective, and light construction, the furnance of the invention has a plastic outer housing, connected by securing elements to the inner housing; the plastic elements have a shell-shaped configuration, so that they define a hollow space surrounding the inner housing, at least adjacent the sidewalls of the outer housing. The hollow space serves as an insulator, minimizing the need for other insulating materials.

10 Claims, 3 Drawing Sheets

DENTAL FURNACE WITH METALLIC INNER HOUSING, PLASTIC OUTER HOUSING, AND AIR SPACE THEREBETWEEN

FIELD OF THE INVENTION

The present invention relates generally to a dental furnace for heat treatment of dental materials and dental components at temperatures above 100° C., and, more particularly, to one with an insulated furnace compartment which can be sealed by a door. The furnace compartment has a housing suspended from an inner metal housing, which in turn is supported by a multi-part outer housing. The furnace door is pivotably secured on the inner housing.

BACKGROUND

A similar dental furnace is known from the present assignee's product brochure no. 90 590 /D 260 S K dt, whose title translates into English as "Silicoater MD, the Kulzer Silicoater Method for Manufacture of a Fissure-Free Plastic-to-Metal Bond in Dentistry."

Such furnaces are installed for firing of dental materials at temperatures up to 400° C. The known furnaces have a furnace or oven compartment which is suspended on the front, where the door also hangs. Between the oven compartment and the front, a frame of aluminum is inserted, as an intermediate component. The actual housing consists of an inner housing of sheet metal, which in turn is clothed by an outer housing of sheet metal. The inner and outer housings rest, at their connection spots, with their surfaces directly contacting. This results in heat conduction from the inner housing to the outer housing, leading the outer housing to heat up severely. In order to avoid excessive heating of the front wall, some insulating material, such as glass wool, is placed between the inner housing and the outer housing. The same steps, i.e. insulating components, are used on the upper surface of the housing and on a sidewall which supports the electronic control units of the furnace. In order to carry heat out of the inner compartment, ventilating slots are provided at the top side and the rear side of the housing. This dental furnace has performed well in service. Nevertheless, the complicated housing structure makes its manufacture expensive, and its severe heating causes certain disadvantages, especially the tendency to heat up the environment surrounding the oven. In dental laboratories, where one typically stores and works with plastic materials having a tendency to harden or cure under the influence of heat, the excess heat output of the prior art furnace can be particularly disadvantageous.

THE INVENTION

Accordingly, it is among the objects of the present invention to provide an improved dental furnace, for heat treatment of dental materials and dental components, which has a simple, cost-effective, and lightweight structure, yet satisfies the performance requirements in the temperature range up to 400° C. for such firing furnaces.

Briefly, the improved furnace of the present invention features an inner metal housing, and an outer housing whose heat-conductive contact with the inner housing is minimized. A hollow airspace between the inner and outer housings provides sufficient thermal insulation without additional packing. The outer housing is not subjected to much heat, so it can be made of plastic, which is lightweight and inexpensive to mold. Preferably, the plastic parts are shell-shaped to lock together. The shell-shaped plastic parts are secured to the inner metal housing using simple rods or spacers, which can be molded onto the plastic parts. Through the shaping of the individual plastic parts in the form of shells, i.e. with at least partially extending circumferential edges or side flanges, a hollow airspace is defined, which assures sufficient spacing of the actual furnace outer surfaces or walls from the hot walls of the inner metal housing.

Preferably, both sidewalls and the upper cover plate are manufactured as identical components in such a structure. These identical components may simultaneously serve as parts of the visible outer housing. The front wall and back or rear wall can rest against or on these plastic parts, i.e. the two sidewalls and upper cover. Preferably, the outer housing's front wall and rear wall are screwed onto the inner housing's front wall and rear wall. The sidewall and cover elements have insertable flanges, tabs, or rod extensions which can be interengaged with the front and rear walls, so that screwing on of the front and rear walls simultaneously clamps the sidewall and cover elements in place.

It has been found that such a structure of the dental furnace renders additional packing, of insulation between the inner metal housing and the outer plastic housing, unnecessary. If desired, ventilating slots can be provided in the cover and both sidewalls, but these are not necessary.

Supplemental ventilating slots are particularly unnecessary if, as in the preferred embodiment, the rear wall of the outer housing is formed with a duct for mounting a fan. Preferably, the duct or tube is molded as part of the plastic rear wall. In order to assure good feeding of air, this tubular duct projects through a corresponding hole or opening in the rear wall of the inner housing. To prevent direct contact and resulting heat conduction, the diameter of the inner housing rear wall is dimensioned slightly larger than the outer diameter of the duct. The fan serves to provide supplemental cooling of the interior space of the dental furnace, in which the actual furnace compartment is located.

Another critical location for heat conduction between the inner metal housing and the outer plastic housing is adjacent the access opening of the inner housing and the access opening of the furnace compartment housing. For this reason, it is desirable to place in this area an insulating frame element which surrounds the furnace compartment opening. Preferably, this frame element is a fiber-cement composite element which consists essentially of mica, quartz, cement and glass fibers. Of course, other heat-resistant composites now known or hereafter discovered would probably also be suitable. It has been found that such a frame element provides sufficient heat insulation between inner housing and outer housing that the remaining heat conduction from the inner housing or from the area of the furnace compartment to the outer plastic housing is small enough to be disregarded.

In order to form the inner housing most simply and easily, a piece of sheet metal is bent into the shape of a letter U, with the uprights serving as the front and rear walls, and the connecting horizontal segment serving as the furnace floor. The front wall features a corresponding furnace compartment opening, which corresponds at least to the opening of the furnace compartment, while the rear wall, in the event a fan is built into the dental furnace, features a corresponding hole for receiving the tubular plastic duct. In order to stabilize the two metal sheet uprights with respect to each other, further metal sheet side panels can be attached. Preferably, the outer surface of one side panel serves as a mounting surface for the electrical and electronic supply and control elements, e.g. a PC board, and power supply components. Further, in a particularly simple and lightweight embodiment, a connection of the front and rear walls can be accomplished using spacer bars screwed at respective ends to upper portions of the front and rear walls. These bars or rods are preferably profiled bars having one or more longitudinally extending grooves, into which the edges or corners, of the plastic part forming the cover, can engage. In this way, the cover can be fixed in position without additional screws. A further groove can serve to receive corresponding corners or edges of the shell-shaped plastic parts forming the sidewalls, or to fix in position the sheet metal inner sidewalls at the upper corners.

DRAWINGS

FIG. 1 is a perspective view of the dental furnace of the present invention, with its door open; and FIG. 2 is an exploded perspective view of the furnace, showing the individual components which form the inner housing, the outer housing, the furnace door, and the furnace interior; and FIG. 3 is a vertical cross-section through the furnace, showing the fan duct at left and the door handle at right.

DETAILED DESCRIPTION

Figure 1:
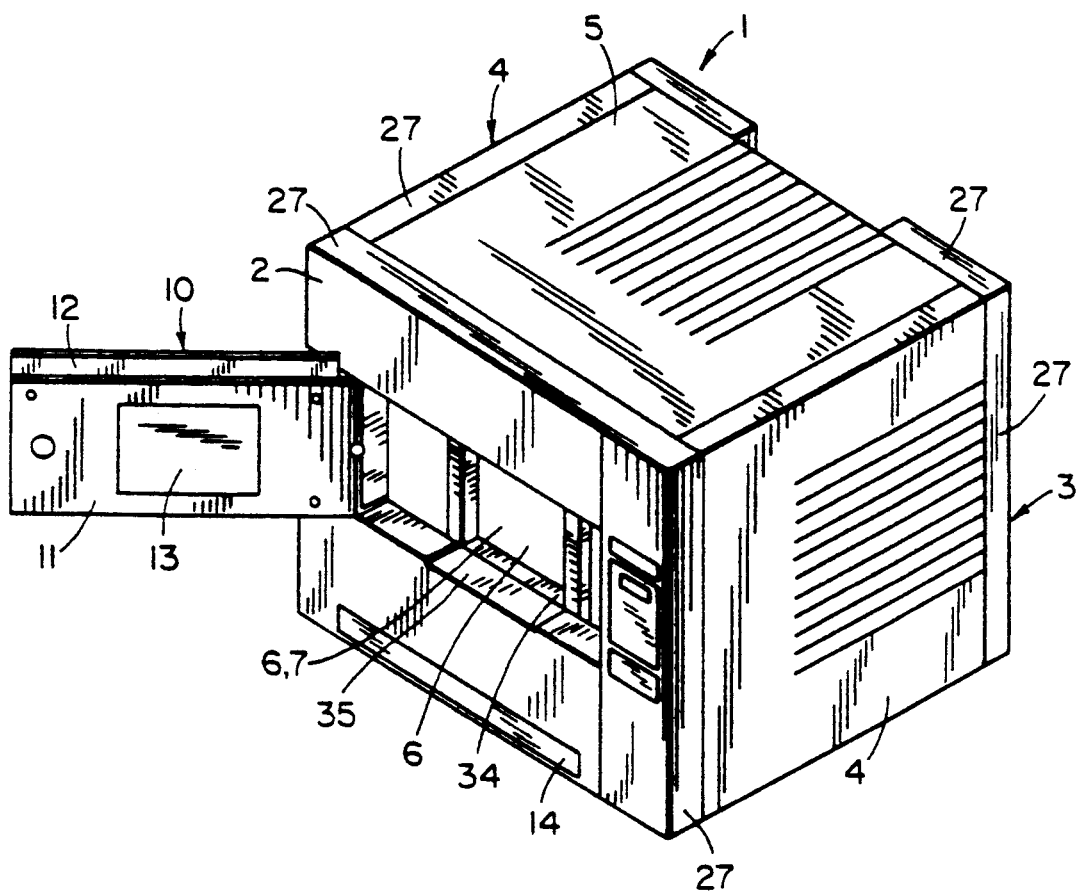

As shown in FIG. 1, the dental furnace of the present invention features an outer housing 1 with a front wall 2, a rear wall 3, two sidewalls 4, and an upper cover 5. These components 2, 3, 4, 5 of outer housing 1 preferably comprise plastic material in the form of shell-shaped plastic parts. Front wall 2 features an access opening 6 which can be closed or sealed by a furnace door 10. Access opening 6 provides access to the interior 7 of a furnace housing 8 of a furnace 9. Furnace door 10 consists essentially of three parts, namely a carrier plate 11, a faceplate 12 covering the outer face of the carrier plate 11, and a metal door plate 13 which, in the closed state, serves as part of the furnace chamber wall. Metal plate 13 is spaced from carrier plate 11 by spacer bars, not shown. At the underside of front wall 2, a slide-out metal shelf 14 is provided for temporary placement of hot items being removed from the furnace.

Figure 2:
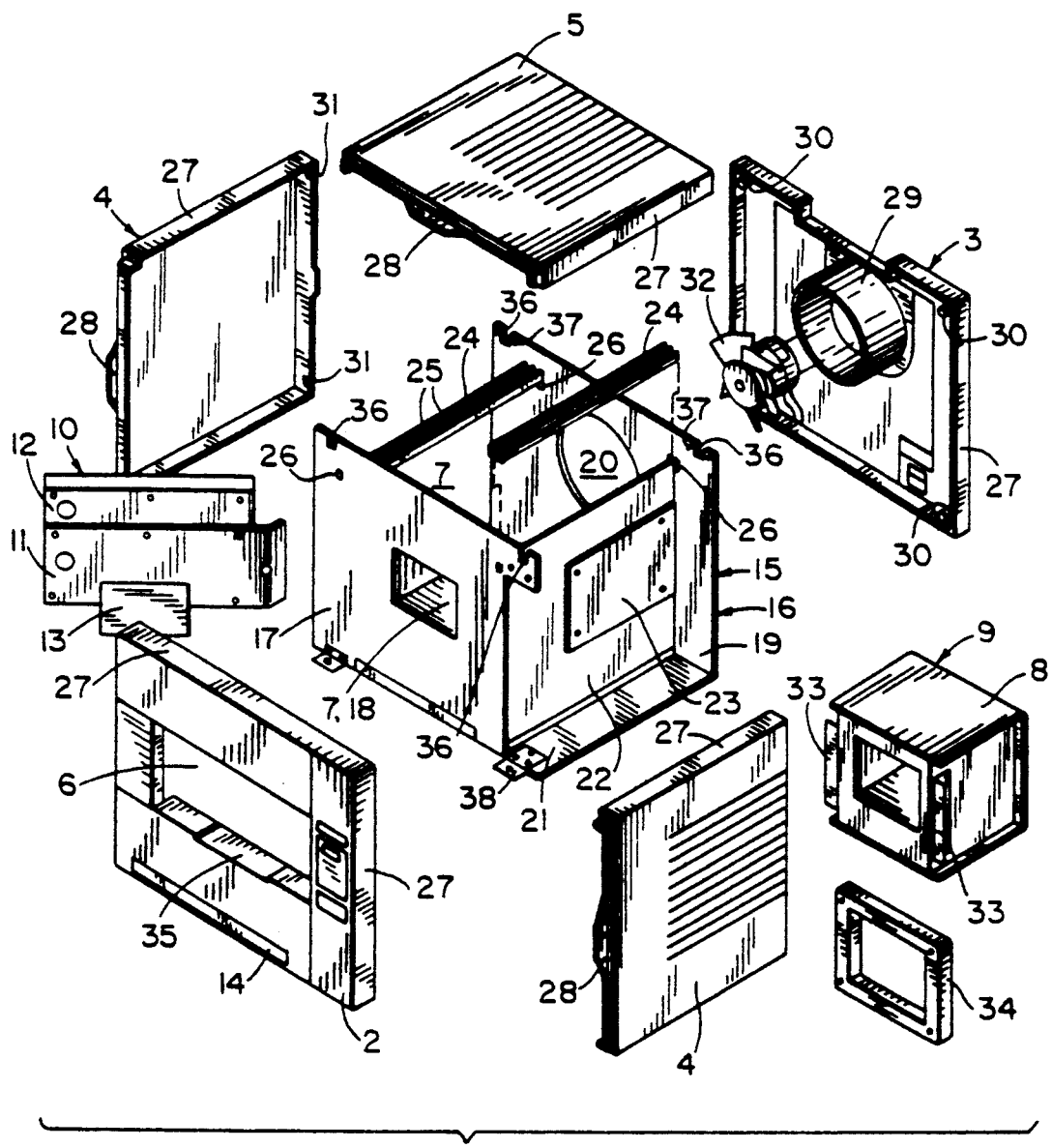
Figure 3:
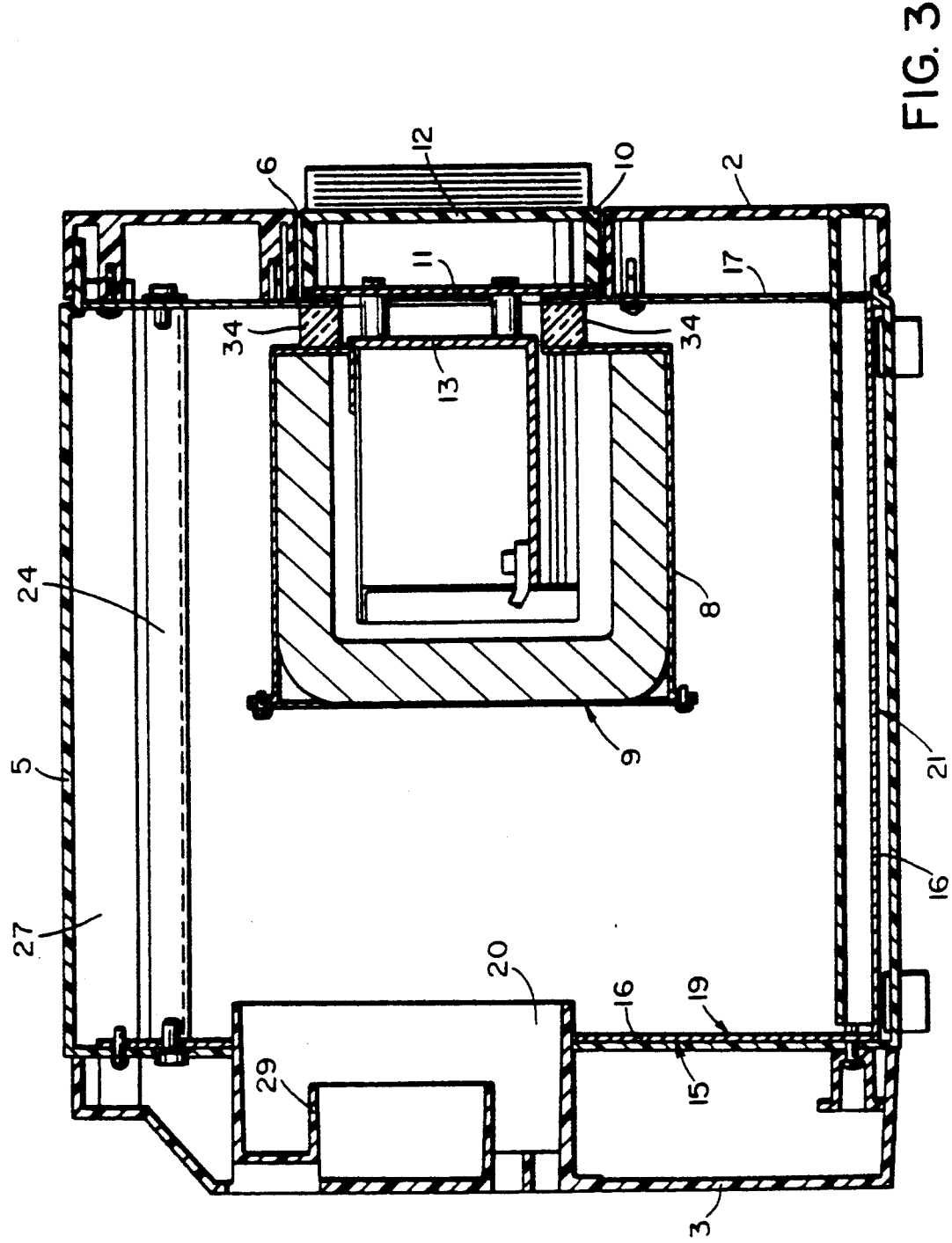

As shown in FIG. 2, the supporting elements of the dental furnace form an inner housing 15, formed largely by a metal sheet 16 bent in a U-shape. The upwardly extending "arms" of the U define a front wall 17, formed with a generally rectangular furnace opening 18, and a rear wall 19, formed with a generally circular opening 20. The connecting base sheet 21, which connects front wall 17 and rear wall 19 to each other, defines the bottom or floor of the dental furnace. On each side, front wall 17 and rear wall 19 are connected by a metal side sheet 22 which, as shown, is spaced slightly inward from the outer corners of walls 17, 19. On the outer face of sheet 22 are mounted the electrical and electronic supply components, such as the power supply for the furnace heating elements. For example, a circuit board 23 can be screwed on as shown.

In order to provide further stabilization, the upper edges of the arms of U-shaped sheet 16, i.e. of front wall 17 and rear wall 19, are connected by spacer bars 24. These spacer bars have a profile featuring longitudinally extending grooves 25; preferably, each spacer rod 24 has on its upper side two or three such grooves 25. These spacer rods are, on the one hand, fitted at each end into bosses 26 stamped into front wall 17 and rear wall 19, and, on the other hand, screwed to front wall 17 and rear wall 19 by screws, not shown.

Preferably, the two sidewalls 4 and upper cover 5 are injection-molded plastic parts identical to each other, formed on three of their edges with right-angled flanges 27, while the fourth edge, directed toward front wall 2, is open. On the fourth or front edge of each, a lip 28 is molded. Front and rear walls 2, 3 each have on all their edges similar flanges 27, so that they assemble into a closed shell.

In the assembled state, the flanges 27 of upper cover 5 can engage in the innermost grooves 25 of spacer bars 24. Side walls 4 are formed with corresponding grooves on the inner surface of their upper edge flanges 27, so that the sidewalls can securely engage and be suspended in a similar manner, preferably in the outer grooves 25 of spacer rods 24.

Rear wall 3 is preferably molded with a central tubular duct element 29, and with four wells 30 in its corner regions for receiving screws (not shown) which secure it to rear wall 19 of inner housing 15. Simultaneously, these screws and wells 30 serve to lock or clamp in place both side walls 4, which are formed with horizontally extending slots 31 for this purpose. In order to secure side walls 4 in front, their lips 28 are stuck inside flanges 27 of front wall 2 of outer housing 1, so that no fasteners such as screws are needed there. As noted, the rear flanges 27 of side walls 4 are placed so that the screws pass through slots 31 and clamp the edges of the slots when the screws are tightened.

A particularly simple fastening of upper cover 5 is achieved by sticking its front lip 28 into a gap defined between the upper edge of front wall 17 of inner housing 15 and top flange 27 of front wall 2 of outer housing 1, while the other side flanges 27 of cover 5 engage in vertically extending slits 36 formed in the upper edge of rear wall 19 and in the upper edge of front wall 17. Prior to screwing on of rear wall 3, upper cover 5 is screwed with two screws through holes 37, from the backside of rear wall 19 of inner housing 15. This fastening means assures minimal heat transmission between components of inner housing 15 and upper cover 5.

A fan 32 is installed in tubular duct 29, in order to ventilate interior 7 of inner housing 15. The tubular duct 29 is so dimensioned, in its outer diameter, with respect to circular opening 20 in rear wall 19 of inner housing 15, that no points of contact arise between tubular duct 29 (preferably plastic) and circular opening 20 (preferably metal).

The front wall 2 of outer housing 1 has, like rear wall 3, a plurality of wells (not shown) which are used for putting screws into corresponding holes in front wall 17 of inner housing 15. Simultaneously with the screwing on of front wall 2 to inner housing 15, lips 28 of upper cover 5 and side walls 5 are engaged by the side flanges 27 of front wall 2, so that these components also become clamped at the forward side.

For assembly of outer housing 1, therefore, one merely needs to screw front wall 2 and rear wall 3 onto the U-bent inner housing 15 with four screws. For this purpose, the base of inner housing 15 has auxiliary sheetmetal pieces 38 as shown. So that no screws will be visible on the outside of front wall 2, during initial assembly, front wall 2 is screwed onto front wall 17 of inner housing 15; subsequently both side walls 4 and upper cover 5 have their respective lips 28 inserted behind flanges 27 of front wall 2 (slits 31 are provided in flanges 27 for orientation and later clamping) and cover 5 is screwed to rear wall 19 using holes 37. Finally, rear wall 3 is screwed on from outside, which fixes both side walls 4 at their rear side.

The shell-shaped components 2, 3, 4, 5 of outer housing 1 define, by their freely suspended arrangement on inner housing 15, a hollow space therebetween, which permits practically no direct heat transmission between outer housing 1 and inner housing 15. The hollow space forms a sufficient thermal insulation that no insulating materials need to be placed in this hollow space.

The actual furnace 9 has two sidewise-projecting flanges 33 which are screwed to the inside of front wall 17 of inner housing 15, so that it is freely suspended in the interior 7 of inner housing 15. As indicated at lower right in the exploded view of FIG. 2, an insulating frame element 34 is placed between flanges 33 and furnace opening 18, on the front wall 17 of inner housing 15. This frame element 34 forms an insulation bridge between furnace 9 and front wall 17 of inner housing 15. Frame element 34 is a fiber-cement frame, which is made of mica, quartz, cement, and glass fibers. It is very suitable for use as an insulator since it features very high cohesiveness and heat tolerance and low thermal conductivity. Furnace 9 may have, at its front wall, a temperature of over 300° C. At the furnace space housing 8, temperatures up to 100° C. are reached. The access opening 6 on front wall 2, which is surrounded or edged around by side flanges, has a metal plate 35 adjacent the lower side flange 27, in order to protect against damage from dental components removed from the furnace. These side flanges, like the outer flanges 27, form a frame.

As FIG. 2 clearly shows, in the preferred embodiment both sidewalls 4 and upper cover 5 are structurally identical, which substantially reduces manufacturing effort, since for entire outer housing 1, only three different injection-molded plastic parts are needed, except for the faceplate 12 of the door.

Various changes and modifications are possible within the scope of the inventive concept.

We claim:

1. Dental furnace for firing of dental materials and dental components at temperatures exceeding 100° C., comprising
    a multi-part outer housing (1) of plastic components;
    an inner housing (15) of metal;
    a plurality of low-thermal-conductivity connecting means (30) suspending said inner housing within said outer housing;
    an insulated furnace compartment (9) supported by said inner housing (15);
    a door (10-13) pivotably supported by said inner housing;
    wherein said furnace has an opening (18) surrounded by a frame element (34), which in turn is aligned with respective access openings of said inner housing (15) and of a housing (8) of said furnace compartment (9),
    wherein said frame element (34) comprises mica, quartz, cement and glass fiber, and wherein
    said plastic components of said outer housing (1) are shell-shaped and define, at least adjacent their sidewalls (4), a hollow space surrounding said inner housing (15).

2. Dental furnace according to claim 1,
    wherein said outer housing (1) has a rear wall (3) including a tubular element (29) and a fan therein; and
    said inner housing (15) has a rear wall (19) formed with a generally circular hole, aligned with said tubular element.

3. Dental furnace according to claim 1, wherein
    said inner housing (15) is generally U-shaped, with one upright defining a housing front wall (17), another upright defining a housing rear wall (19), and a connecting portion (22) defining a furnace floor.

4. Dental furnace according to claim 3, wherein
    said uprights have corners at their respective upper ends, and said corners are connected by at least one spacer bar (24).

5. Dental furnace according to claim 4, wherein
    each spacer bar (24) is formed with a plurality of longitudinal grooves into which cover (5) and sidewall (4) elements of said outer housing (1) engage and are suspended.

6. Dental furnace according to claim 1, wherein
    said outer housing (1) includes sidewall (4) and cover (5) elements formed with flanges (27); and
    said flanges (27) are formed with slits (31) for engagement with said inner housing (15).

7. Dental furnace according to claim 6, wherein
    each of said sidewall (4) and cover (5) elements is formed with a lip (28) which interengages a flange (27) of at least one other of said elements.

8. Dental furnace according to claim 7, wherein
    said lips (28) are formed on adjacent, opposing edges of said elements.

9. Dental furnace according to claim 6, wherein
    said slits (31) are formed in flanges (27) which point toward said rear wall (3) of said outer housing (1).

10. Dental furnace according to claim 8, wherein
    said cover (5) and said sidewall (4) elements have essentially identical structures.

* * * * *